US00PP23465P2

(12) United States Plant Patent
Arts

(10) Patent No.: US PP23,465 P2
(45) Date of Patent: Mar. 12, 2013

(54) ***HYDRANGEA* PLANT NAMED 'AVANTGARDE'**

(50) Latin Name: *Hydrangea macrophylla*
Varietal Denomination: Avantgarde

(75) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 102 days.

(21) Appl. No.: 13/068,375

(22) Filed: May 9, 2011

(51) Int. Cl.
*A01H 5/00* (2006.01)

(52) U.S. Cl. ..... Plt./250

(58) Field of Classification Search ..... Plt./250
See application file for complete search history.

*Primary Examiner* — June Hwu

(74) *Attorney, Agent, or Firm* — C. A. Whealy

(57) ABSTRACT

A new and distinct cultivar of *Hydrangea* plant named 'Avantgarde', characterized by its upright plant habit; strong and sturdy stems; freely flowering habit with numerous sterile flowers per inflorescence; large mophead-type inflorescences with light red purple-colored flowers; and short production time as a cooling treatment is not required for flower development.

1 Drawing Sheet

Botanical designation: *Hydrangea macrophylla.*
Cultivar denomination: 'AVANTGARDE'.

BACKGROUND OF THE INVENTION

The present invention relates to a new and distinct cultivar of *Hydrangea* plant, botanically known as *Hydrangea macrophylla* and hereinafter referred to by the name 'Avantgarde'.

The new *Hydrangea* plant is a product of a planned breeding program conducted by the Inventor in Aalsmeer, The Netherlands. The objective of the breeding program was to create new freely branching *Hydrangea* plants with strong and sturdy stems, large inflorescences, attractive flower color and that do not require a cooling treatment for flower development.

The new *Hydrangea* plant originated from a cross-pollination made by the Inventor in April, 2007 in De Kwakel, The Netherlands, of a proprietary selection of *Hydrangea macrophylla* identified as code number 206155-01, not patented, as the female, or seed, parent with a proprietary selection of *Hydrangea macrophylla* identified as code number 206014, not patented, as the male, or pollen, parent. The new *Hydrangea* plant was discovered and selected by the Inventor as a single flowering plant from within the progeny of the stated cross-pollination in a controlled greenhouse environment in De Kwakel, The Netherlands in April, 2009.

Asexual reproduction of the new *Hydrangea* plant by vegetative cuttings in a controlled environment in De Kwakel, The Netherlands since June, 2009 has shown that the unique features of this new *Hydrangea* plant are stable and reproduced true to type in successive generations.

SUMMARY OF THE INVENTION

Plants of the new *Hydrangea* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Avantgarde'. These characteristics in combination distinguish 'Avantgarde' as a new and distinct *Hydrangea* plant:

1. Upright plant habit.
2. Strong and sturdy stems.
3. Freely flowering habit with numerous sterile flowers per inflorescence.
4. Large mophead-type inflorescences with light red purple-colored flowers.
5. Short production time as a cooling treatment is not required for flower development.

Plants of the new *Hydrangea* differ from plants of female parent selection primarily in flower size as plants of the new *Hydrangea* have larger flowers than plants of the female parent selection.

Plants of the new *Hydrangea* differ from plants of male parent selection primarily in flower coloration as plants of the male parent selection have darker-colored flowers. In addition, plants of the new *Hydrangea* do not require a cooling treatment for flower development whereas plants of the male parent selection require a cooling treatment for flower development.

Plants of the new *Hydrangea* can be compared to plants of the *Hydrangea* 'Pink Sensation', not patented. Plants of the new *Hydrangea* differ from plants of 'Pink Sensation' in the following characteristics:

1. Plants of the new *Hydrangea* are taller than plants of 'Pink Sensation'.
2. Plants of the new *Hydrangea* have larger leaves than plants of 'Pink Sensation'.
3. Plants of the new *Hydrangea* have smaller flowers than plants of 'Pink Sensation'.
4. Plants of the new *Hydrangea* have larger inflorescences than plants of 'Pink Sensation'.
5. Plants of the new *Hydrangea* do not require a cooling treatment for flower initiation whereas plants of 'Pink Sensation' require a cooling requirement for flower development.

BRIEF DESCRIPTION OF THE PHOTOGRAPH

The accompanying colored photograph illustrates the unique appearance of the new *Hydrangea* plant showing the colors as true as it is reasonably possible to obtain in colored reproductions of this type. Colors in the photograph may differ from the color values cited in the detailed botanical description which accurately describe the colors of the new *Hydrangea* plant. The photograph comprises a side perspective view of a typical flowering plant of 'Avantgarde' when the flowers are opening (left) and a typical flowering plant of 'Avantgarde' when the flowers are fully opened (right).

DETAILED BOTANICAL DESCRIPTION

Plants used in the aforementioned photograph and in the following description were grown during the winter in 15-cm containers in a glass-covered greenhouse in De Kwakel, The Netherlands and under environmental and cultural conditions which closely approximate commercial *Hydrangea* production conditions. During the production of the plants, day and night temperatures averaged 17° C. Plants were not pinched and were grown as single-stem plants. Plants of the new *Hydrangea* were 22 weeks old when the photograph and description were taken. In the following description, color references are made to The Royal Horticultural Society Colour Chart, 1995 Edition, except where general terms of ordinary dictionary significance are used.

Botanical description: *Hydrangea macrophylla* 'Avantgarde'.

Parentage:

*Female, or seed, parent*.—Proprietary selection of *Hydrangea macrophylla* identified as code number 206155-01, not patented.

*Male, or pollen, parent*.—Proprietary selection of *Hydrangea macrophylla* identified as code number 206014, not patented.

Propagation:

*Type cutting*.—By vegetative cuttings.

*Time to initiate roots, summer*.—About 14 days at temperatures of 23° C.

*Time to initiate roots, winter*.—About 18 days at temperatures of 18° C.

*Time to produce a rooted young plant, summer*.—About four weeks at temperatures of 23° C.

*Time to produce a rooted young plant, winter*.—About five weeks at temperatures of 18° C.

*Root description*.—Thick; whitish brown in color.

*Rooting habit*.—Freely branching; dense.

Plant description:

*Form/growth habit*.—Upright plant habit; conical in shape; strong and sturdy stems; rapid growth rate and vigorous growth habit.

*Plant height*.—About 60 cm.

*Plant diameter or area of spread*.—About 40 cm.

*Internode length*.—About 5 cm to 7 cm.

*Stem texture*.—Smooth, glabrous.

*Strength*.—Strong and sturdy.

*Color*.—Close to 145A; lenticels, close to 187A.

Foliage description:

*Arrangement*.—Opposite, simple.

*Length*.—About 16 cm to 18 cm.

*Width*.—About 12 cm.

*Shape*.—Ovate.

*Apex*.—Acute.

*Base*.—Obtuse.

*Margin*.—Serrate.

*Texture, upper and lower surfaces*.—Rugose, glabrous.

*Venation pattern*.—Pinnate.

*Color*.—Developing leaves, upper and lower surfaces: Darker than 144A. Fully expanded leaves, upper surface: Close to 147A; venation, close to 145C. Fully expanded leaves, lower surface: Close to 147B; venation, close to 145B.

*Petiole*.—Length: About 2.5 cm. Diameter: About 7 mm. Texture, upper and lower surfaces: Smooth, glabrous. Color, upper surface: Close to 145C. Color, lower surface: Close to 145B.

Flower description:

*Flower type and habit*.—Single sterile and fertile flowers arranged on terminal mophead-type panicles; panicles globular in shape; flowers face upright to outward.

*Fragrance*.—None detected.

*Natural flowering season*.—Short production time as a cooling treatment is not required for flower development; continuous flowering during the summer in Northern Europe.

*Flower longevity*.—Sterile flowers last about four months on the plant, sterile flowers persistent; fertile flowers last about one week on the plant, fertile flowers not persistent.

*Quantity of flowers*.—Freely flowering habit; about 1,000 sterile flowers per panicle and about 20 fertile flowers per panicle.

*Panicle height*.—About 18 cm.

*Panicle diameter*.—About 24 cm.

*Sterile flower diameter*.—About 2.5 cm.

*Sterile flower depth* (*height*).—About 1 cm.

*Fertile flower diameter*.—About 5 mm.

*Fertile flower depth* (*height*).—About 3 mm.

*Petals, sterile flowers only, fertile flowers without petals*.—Quantity and arrangement: About four or five arranged in a single whorl. Length: About 1 mm. Width: About 1 mm. Shape: Ovate. Apex: Acute. Base: Attenuate. Margin: Entire. Texture, upper and lower surfaces: Smooth, glabrous. Color: When opening, upper and lower surfaces: Close to 1D. Fully opened, upper and lower surfaces: Close to 73B; color becoming closer to 145B to 145C with development.

*Sepals, sterile flowers*.—Quantity and arrangement: About four or five arranged in a single whorl. Length: About 1.5 cm. Width: About 1.5 cm. Shape: Obovate. Apex: Retuse. Base: Cuneate. Margin: Entire. Texture, upper and lower surfaces: Smooth, glabrous. Color: When opening, upper and lower surfaces: Close to 1D. Fully opened, upper and lower surfaces: Close to 69D; towards the base, close to 73B.

*Sepals, fertile flowers*.—Quantity and arrangement: About six arranged in a single whorl. Length: About 2 mm. Width: About 1.5 mm. Shape: Ovate. Apex: Acute. Base: Obtuse. Margin: Entire. Texture, upper and lower surfaces: Smooth, glabrous. Color, upper surface: Close to 78C. Color, lower surface: Close to 78D.

*Pedicels, sterile flowers*.—Length: About 2 cm. Diameter: About 6 mm. Strength: Strong. Texture: Smooth, glabrous. Color: Close to 145B; spots, close to 187A.

*Pedicels, fertile flowers*.—Length: About 3 mm. Diameter: About 1 mm. Strength: Strong. Texture: Smooth, glabrous. Color: Close to 186C to 186D.

*Reproductive organs, fertile flowers only; sterile flowers without reproductive organs*.—Stamens: Quantity per flower: About six. Anther shape: Conical. Anther length: About 1 mm. Anther color: Close to 89B. Pollen amount: Abundant. Pollen color: Close to 155D. Pistils: Pistil quantity per flower: About three. Pistil length: About 1 mm. Stigma shape: Oval. Stigma color: Close to 186D. Style length: About 0.5 mm. Style color: Close to 186D. Ovary color: Close to 186D.

*Seeds*.—Length: About 0.5 mm. Diameter: About 0.1 mm. Color: Close to 200C.

Disease/pest resistance: Under commercial production conditions, plants of the new *Hydrangea* have not been observed to be resistant to pathogens or pests common to *Hydrangea*.

Temperature tolerance: Plants of the new *Hydrangea* have been shown to be tolerant to temperatures ranging from about 3° C. to about 38° C.

It is claimed:

1. A new and distinct *Hydrangea* plant named 'Avantgarde' as illustrated and described.

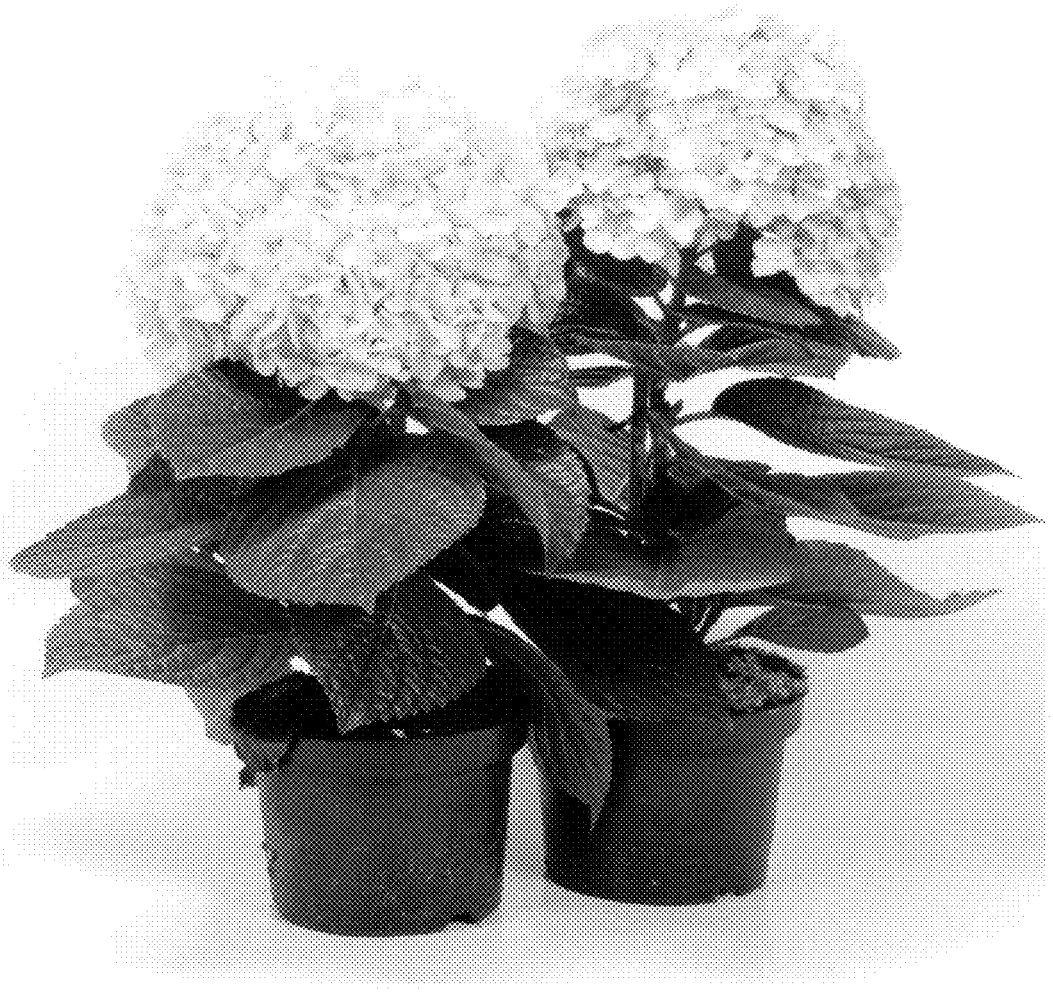

* * * * *